United States Patent [19]

Seidel et al.

[11] Patent Number: 5,620,567
[45] Date of Patent: Apr. 15, 1997

[54] PROCESS FOR THE REMOVAL OF ALDEHYDES AND ACETALS FROM INDUSTRIALLY PREPARED ACETIC ACID

[75] Inventors: Andreas Seidel, Köln; Alfred Hauser, Erftstadt; Peter Prinz, Hürth, all of Germany

[73] Assignee: Hoechst Aktiengesellschaft, Frankfurt am Main, Germany

[21] Appl. No.: 283,280

[22] Filed: Jul. 29, 1994

[30] Foreign Application Priority Data

Aug. 12, 1993 [DE] Germany ............ 43 27 011.5

[51] Int. Cl.⁶ .................. B01D 3/34; C07C 51/44
[52] U.S. Cl. .................. 203/34; 203/35; 203/64; 203/92; 203/95; 203/96; 562/608
[58] Field of Search .................. 203/34, 35, 64, 203/92, 95, 96; 568/913; 562/607, 608

[56] References Cited

U.S. PATENT DOCUMENTS

| | | | |
|---|---|---|---|
| 2,295,618 | 9/1942 | Wulff et al. | 203/35 |
| 2,382,181 | 8/1945 | Staudinger et al. | 203/35 |
| 2,867,655 | 1/1959 | Othmer | 203/34 |
| 3,196,176 | 7/1965 | Howell | 203/35 |
| 3,709,795 | 1/1973 | Singleton . | |
| 3,772,156 | 11/1973 | Johnson et al. | 203/34 |
| 3,878,057 | 4/1975 | Mannsfeld | 203/34 |
| 4,061,546 | 12/1977 | Singleton . | |
| 4,110,372 | 8/1978 | Hey et al. | 562/608 |
| 4,383,893 | 5/1983 | Karbel et al. | 203/41 |
| 4,388,154 | 6/1983 | Hochstein et al. | 203/35 |

FOREIGN PATENT DOCUMENTS

| | | | |
|---|---|---|---|
| 2104828 | 6/1980 | Germany . | |
| 1699950 | 12/1991 | U.S.S.R. | 203/35 |

OTHER PUBLICATIONS

CAS 108: 2065 45.
CAS 73: 24918.

*Primary Examiner*—Virginia Manoharan
*Attorney, Agent, or Firm*—Connolly & Hutz

[57] ABSTRACT

A process for the removal of aldehydes and acetals from industrially prepared acetic acid, wherein the contaminated acetic acid is reacted in the presence of a Brönstedt acid and 0.05 to 1% by weight of water and, if required, of 3 to 10 equivalents, calculated on aldehyde and acetal, of a high boiling polyhydric alcohol, and isolating the purified acetic acid by fractional distillation.

4 Claims, No Drawings

PROCESS FOR THE REMOVAL OF ALDEHYDES AND ACETALS FROM INDUSTRIALLY PREPARED ACETIC ACID

The present invention relates to a process for the removal of aldehydes and acetals from industrially prepared acetic acid as arises, in particular, in the catalytic oxidation of acetaldehyde and the carbonylation of methanol.

Industrially prepared acetic acid, depending on the production process, contains impurities such as formic acid, acetates, formates, acetaldehyde and formaldehyde. To achieve higher specification grades such as, for example, the quality "chemically pure", the content of these impurities in the acetic acid must be reduced as far as possible. An analytical measure for this is the chromic acid test by the analytical method specified in the Deutsches Arzneibuch 10 (1991), by which the content of oxidizable impurities can be quantitatively determined in the acetic acid.

In addition to the said compounds which can be separated off by distillation, there are also impurities which boil in the range of the boiling point of acetic acid and can therefore not be removed by distillation. These are principally the addition or condensation products of aldehydes, in particular oxidizable hemiacetals and complete acetals such as, for example, formaldehyde methyl acetyl acetal (methoxymethyl acetate; b.p. 117°–118° C.) or acetaldehyde diacetyl acetal (1,1-diacetoxyethane; b.p. 169° C.). Since these compounds are also determined by the chromic acid test, only unsatisfactory yields of chemically pure acetic acid in conformance with specifications are obtainable by means of a distillation.

For the removal of the aldehydes and acetals, therefore, potassium dichromate has been proposed in U.S. Pat. No. 4,061,546 and potassium permanganate has been proposed in DE-A-21 04 828 as oxidants. Pure acetic acid is then obtained in a downstream distillation.

A disadvantage of these processes is the use of expensive oxidants which lead to heavy-metal-containing distillation residues, the disposal of which is problematic. In addition, toxic products can be formed, for example formic acid from formaldehyde, in such oxidation processes.

The object was therefore to find an inexpensive process which makes possible as complete as possible a removal of aldehydes and acetals from industrially prepared acetic acid, in which there are no disposal problems and no toxic products are formed.

Surprisingly, the object could be achieved according to the invention by reacting the industrially prepared acetic acid in the presence of a Brönstedt acid and 0.05 to 1% by weight of water and, if required, of 3 to 10 equivalents, calculated on aldehyde and acetal, of a high-boiling polyhydric alcohol having the general structural member

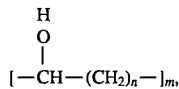

in which n is an integer from 0 to 3 and m is an integer greater than 3, at temperatures of 50° to 118° C. for a period of 1 to 5 hours, and then isolating the pure acetic acid from the reaction product by fractional distillation.

The process of the invention can, furthermore, if desired, have the feature that
a) the Brönstedt acid used is a substance selected from the group consisting of sulfuric acid, methanesulfonic acid, toluenesulfonic acid or phosphoric acid in an amount of 0.005 to 0.05 mol/l of contaminated acetic acid;
b) the high-boiling polyhydric alcohol used is a substance selected from the group consisting of poly(vinyl alcohol), cane sugar and dextrose, starch or cellulose.

The industrially prepared acetic acid is advantageously reacted with an excess of the high-boiling polyhydric alcohol in order to ensure as complete as possible a removal of the aldehydes and acetals.

A polyhydric alcohol which is obtained by hydrolysis of poly(vinyl acetate) in methanol can advantageously be used.

If only a partial purification of the industrial acetic acid is desired, the addition of the high-boiling polyhydric alcohol can be dispensed with. Example 1 shows the cleaning effect without addition of high-boiling polyhydric alcohol.

The Examples 1, 2 and the comparative example were carried out with an industrially prepared acetic acid which contained the following impurities:

| | | |
|---|---|---|
| Acetic acid content | 99.6 | [% by weight] |
| Water | 0.036 | [% by weight] |
| Formaldehyde | 57 | [ppm] |
| Acetaldehyde | 1.8 | [ppm] |
| Methyl acetate | 59 | [ppm] |
| Ethyl acetate | 151 | [ppm] |
| Isopropyl acetate | 40 | [ppm] |
| Methoxymethyl acetate | 130 | [ppm] |
| Chromic acid test, according to Schering (% kg denotes "per 100 kg") | 80 | [g of CrO$_3$ % kg] |

The invention is described in more detail by means of the examples.

Example 1 (without addition of polyhydric alcohol)

5 kg of industrially prepared acetic acid, together with 3.5 g of water and 5 g of methanesulfonic acid, were placed in the evaporator of a vapor baffle plate column having 20 plates and were refluxed for 3 h at an overhead pressure of 350 mbar. The mixture was then fractionally distilled at an overhead pressure of 350 mbar with a reflux ratio decreasing towards the end (10:1 to 2:1). By combining individual fractions, in total, after a low-boiling first runnings of 0.54 kg (including cold trap product), 1.68 kg of acetic acid (33.6% by weight of starting material) were obtained having a chromic acid test of 21 g of CrO$_3$% kg and 2.73 kg of acetic acid (54.6% by weight of starting material) having a chromic acid test <10 g of CrO$_3$% kg.

Example 2 (with addition of polyhydric alcohol)

5 kg of industrially prepared acetic acid, together with 3.5 g of water, 5 g of methanesulfonic acid and 0.9 g of MOWIOL® 10-74 (10-fold equivalent excess calculated on aldehyde and acetal), were refluxed in a 6 l glass flask having an attached 20-plate vapor baffle plate column at an overhead pressure of 350 mbar. for 3 hours at a bottom temperature of 87.5° C. The fractional distillation at a reflux ratio of 10:1 yielded 350 g of an aqueous first runnings having a chromic acid test of 216 g of CrO$_3$% kg. At bottom temperatures between 90° C. and 112° C. (89° C. to 90° C. on plate 10 of the column, overhead temperature 87° C.) with decreasing reflux ratio (10:1 to 2:1), 4520 g of acetic acid were then obtained having a chromic acid test of 7 g of CrO$_3$% kg (DAB 10 quality: <32 g of CrO$_3$% kg) and the analysis listed in Table 1 was obtained. This represents 90% of the acetic acid used. A further 23 g are located in the distillation cold trap, the residue remains as distillation bottom product.

TABLE 1

|  | Purified acetic acid | |
| --- | --- | --- |
| Acetic acid content | 99.8 | [%] |
| Water | 0.18 | [%] |
| Formaldehyde | <10 | [ppm] |
| Acetaldehyde | 0.2 | [ppm] |
| Methyl acetate | <10 | [ppm] |
| Ethyl acetate | <10 | [ppm] |
| Isopropyl acetate | <10 | [ppm] |
| Methoxymethyl acetate | <10 | [ppm] |
| Chromic acid test, according to Schering | 7 | [g of $CrO_3$ % kg] |

Comparative Example
(purification by distillation only)

500 g of industrially prepared acetic acid were placed in the evaporator of a column having 30 plates. Under complete reflux conditions, the evaporator contents were heated to 85° C. at an overhead column pressure of 230 mbar. As soon as the column was in equilibrium, fractional distillation was carried out at a reflux of 6:1. After a first runnings of 83 g was taken off, a fraction was obtained of 167 g having a chromic acid test of <32 g of $CrO_3$% kg. The following 139 g of distillate, with a chromic acid test of <10 g of $CrO_3$% kg, had a further improved purity. Subsequently to this fraction, a further 83 g were obtained having a chromic acid test of <32 g of $CrO_3$% kg. 27 g remained as bottom product. In total, 50.0% of the acetic acid used were obtained having a chromic acid test <32 g of $CrO_3$% kg and 28.0% of the acetic acid used were obtained having a chromic acid test <10 g of $CrO_3$% kg.

We claim:

1. A process for the removal of aldehydes and acetals from industrially prepared acetic acid prepared by catalytic oxidation of acetaldehyde or carbonylation of methanol, consisting essentially of reacting the industrially prepared acetic acid in the presence of a substance selected from the group consisting of methanesulfonic acid, toluenesulfonic acid and phosphoric acid, in an amount of 0.005 to 0.05 mol/l of contaminated acetic acid, at a temperature of 50° to 118° C. for a period of 1 to 5 hours, and isolating purified acetic acid by fractional distillation.

2. The process of claim 1, wherein 0.05 to 1% by weight of water is added to the industrially prepared acetic acid.

3. The process of claim 2, wherein a polyhydric alcohol is added to the industrially prepared acetic acid.

4. A process for the removal of aldehydes and acetals from industrially prepared acetic acid, which comprises reacting the industrially prepared acetic acid in the presence of 0.005 to 0.05 mol/l of contaminated acetic acid of a Brönstedt acid, in the presence of water and in the presence of 3–10 equivalents, based on aldehyde and acetal present in the industrially prepared acetic acid, of a high-boiling polyhydric alcohol selected from the group consisting of poly(vinyl alcohol), cane sugar, dextrose, starch and cellulose, at a temperature of 50° to 118° C. for a period of 1 to 5 hours, and isolating purified acetic acid by fractional distillation.

* * * * *